United States Patent

Carr et al.

[11] Patent Number: 5,980,518
[45] Date of Patent: Nov. 9, 1999

[54] MICROCAUTERY SURGICAL TOOL

[76] Inventors: William N. Carr, 251 S. Mountian Ave., Montclair, N.J. 07042; Lewis T. Ladocsi, 177 Hobart Ave., Short Hills, N.J. 07078

[21] Appl. No.: 08/976,286

[22] Filed: Nov. 21, 1997

Related U.S. Application Data

[63] Continuation-in-part of application No. 08/549,541, Oct. 27, 1995, Pat. No. 5,792,137.

[51] Int. Cl.[6] .................................................. A61B 17/36
[52] U.S. Cl. .............................................. 606/45; 606/29
[58] Field of Search .................................. 606/1, 27–31, 606/45, 41, 169; 604/21, 22

[56] References Cited

U.S. PATENT DOCUMENTS

| | | | |
|---|---|---|---|
| 4,091,813 | 5/1978 | Shaw et al. | 606/29 |
| 4,219,025 | 8/1980 | Johnson | 606/31 |
| 4,850,353 | 7/1989 | Stasz et al. | 606/45 |
| 4,860,744 | 8/1989 | Johnson et al. | 606/29 |
| 4,960,419 | 10/1990 | Rosenberg | 606/45 |
| 5,387,190 | 2/1995 | Gotanda et al. | 604/22 |
| 5,695,510 | 12/1997 | Hood | 606/169 |
| 5,728,089 | 3/1998 | Lal et al. | 606/1 |
| 5,792,137 | 8/1998 | Carr et al. | 606/29 |

*Primary Examiner*—Michael Peffley
*Attorney, Agent, or Firm*—Joseph P. Errico, Esq.

[57] ABSTRACT

A surgical instrument is provided which is formed of a semiconductor substrate material having at least one anisotropically etched sharpened edge and a heating circuit disposed on the substrate. The heating circuits generate heat by means of resistive elements interposed along the circuit path. The substrate material itself may serve as the resistive elements, or resistive layers may be used in the alternative. The resistive heating may be used to heat the sharpened edge directly, or the heating may be thermally isolated from the sharpened edge. The heating circuit may also include a thermal sensor which may be used to control the generation of heat and/or detect damage to the instrument itself. The conformation of the instrument may include a variety of different shapes, including central recesses and windows. The recesses may further include ribs or support members. The substrate may further a suction mechanism for removing fluid which may build up in the vicinity of the surgery.

4 Claims, 6 Drawing Sheets

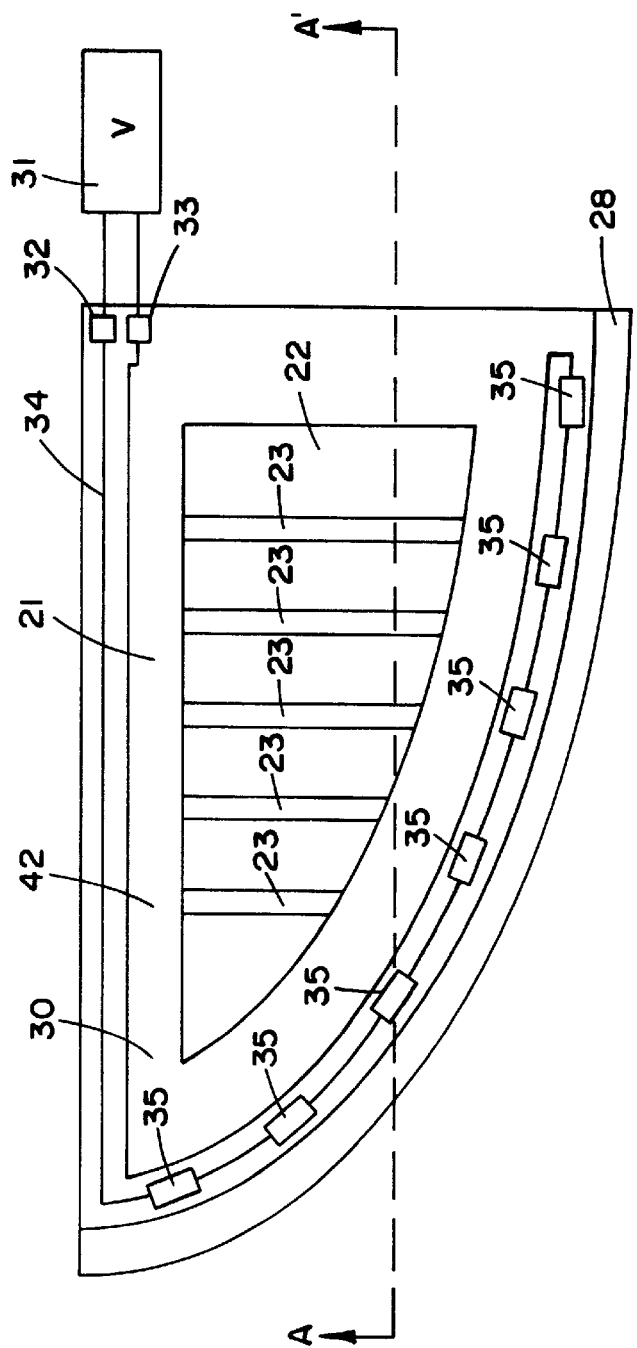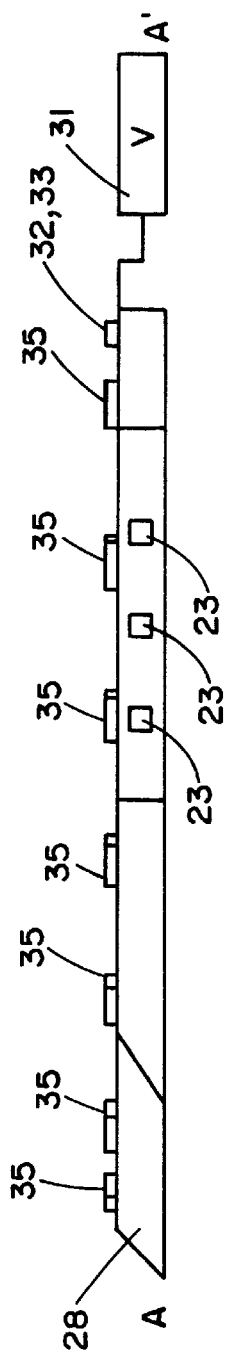

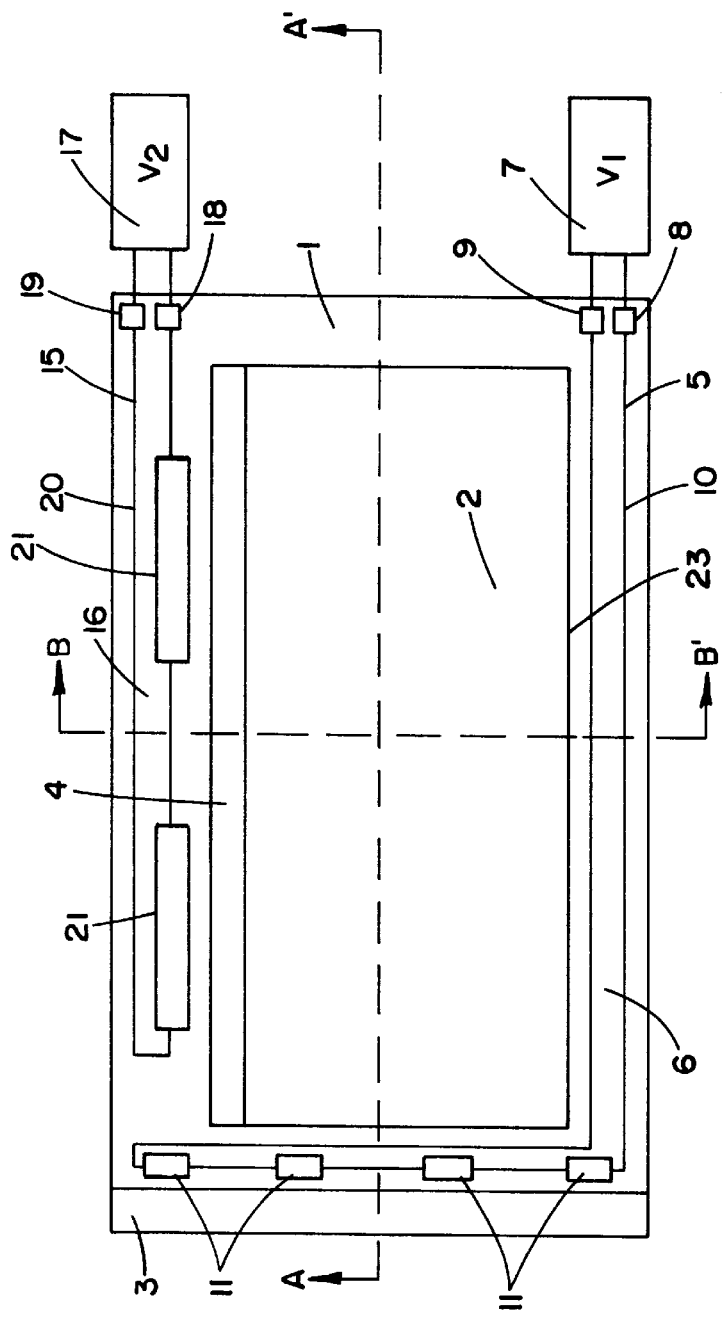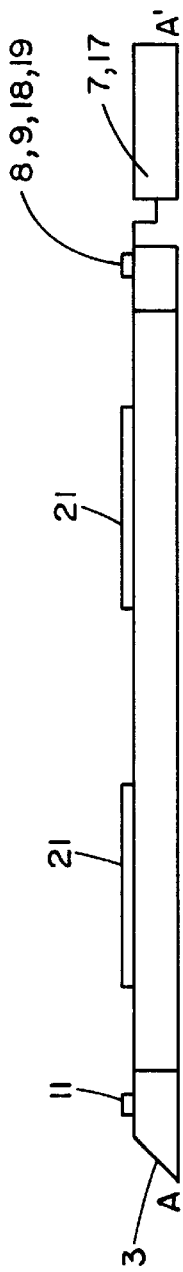
FIG.3
FIG.4

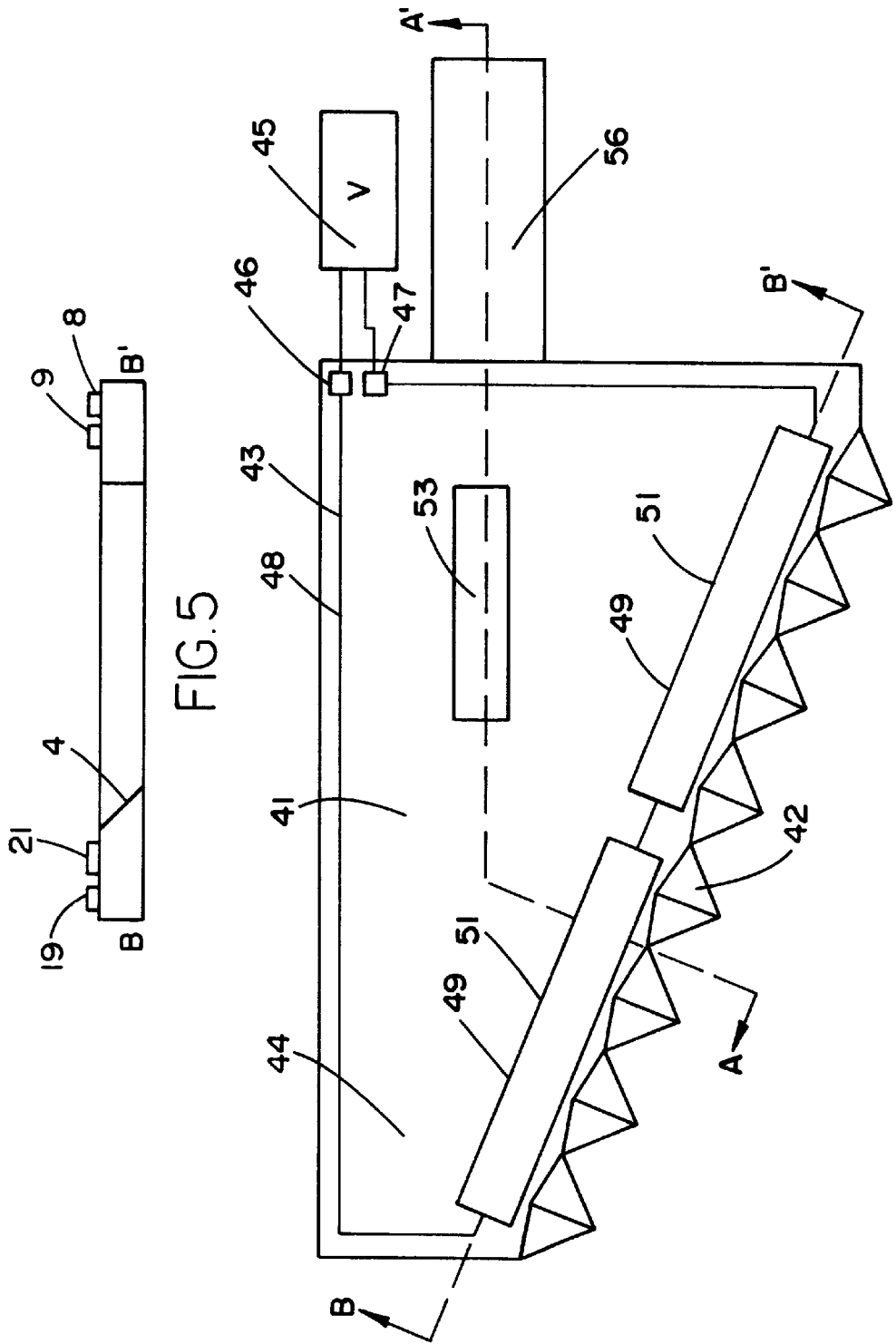

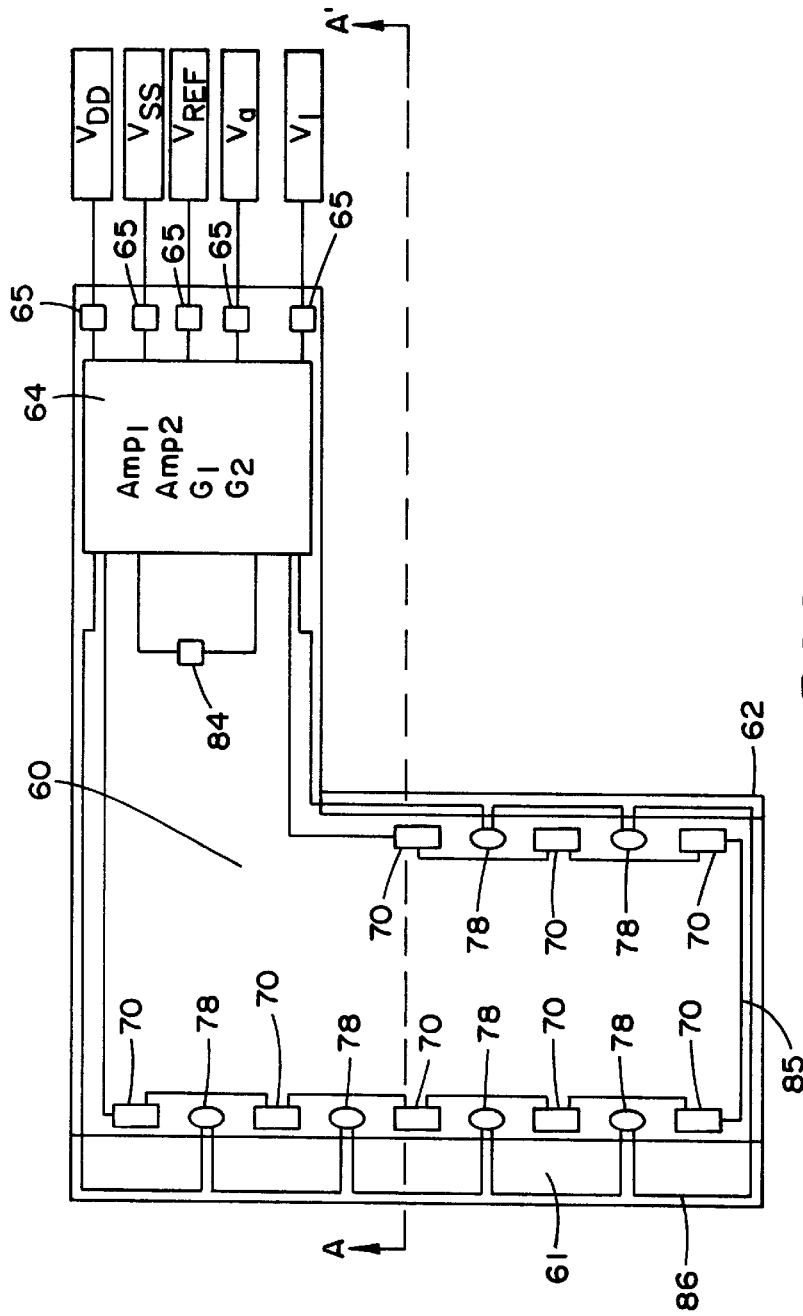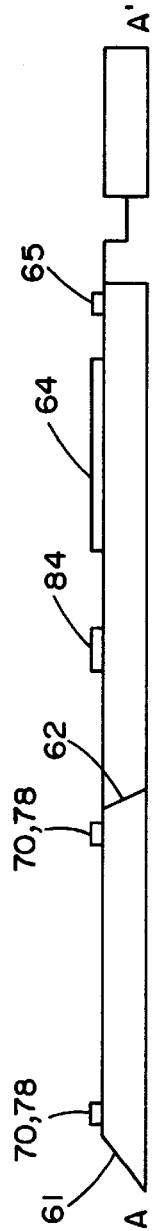
FIG. 9
FIG. 10

MICROCAUTERY SURGICAL TOOL

CROSS-REFERENCE TO RELATED APPLICATION

The present invention is a continuation-in-part of U.S. patent application Ser. No. 08/549,541, entitled "Coagulating Microknife System", filed Oct. 27, 1995, now U.S. Pat. No. 5,792,137, in the names of the inventors of the present invention.

BACKGROUND OF THE INVENTION

1. Field of the Invention

This invention relates to a surgical tool for simultaneously performing precision cutting and cauterizing of targeted tissues, and more specifically to a semiconductor knife constructed by appropriate semiconductor processing methods and techniques, said tool having electrocautery circuits imprinted thereon which are capable of heating at least a portion of the tool to sufficient temperatures to effect precise cauterization of adjacent targeted tissues.

2. Brief Description of the Prior Art

Presently, surgical devices for precision cutting are divided into different classes. Two important classes of such devices are microscalpels and laser scalpels. The former class has traditionally been solely a mechanical device, insofar as its only capacity was to physically separate tissues. This limited capacity, coupled with the unavoidable disruption of blood carrying members, required the use of another surgical tool for stemming the flow of fluids which might be initiated during the cutting. It has long been known that the sufficient application of heat to fluids, such as blood, or the tissue from whence such fluids flow, can cause their coagulation. Electrocautery instruments have been utilized in conjunction with mechanical scalpels to apply the heat necessary to cauterize the targeted tissues. These electrocautery tolos suffer from three substantial drawbacks. The first two of these are related to the surgical use.

First, separate electrocautery and mechanical scalpel devices often requires that the surgeon laboriously changes between using the scalpel and the electrocautery tool during the surgical procedure. Surgeons have found several manual means for overcoming this serious disadvantage, none of which truly reaches the ideal flexibility of the present invention. One such manual solutions is to have two surgeons working in the same surgical field, the first manipulating the cutting instrument, and the second manipulating the cauterizing instrument. For obvious reasons, including wasted expertise and the requirement of unnecessary coordinated activity, this solution is the least economically desirable, and is also the least efficient insofar as it often requires verbal communication between the two surgeons during periods of time when more critical information should be discussed.

A second solution which surgeons have discovered to attempt to overcome the serious drawbacks of separate scalpel and electrocautery instrumentation is to hold both instruments in the same hand, or at least in separate hands. Again, for obvious reasons, requiring a surgeon to hold both instruments in one hand, or at best having the two instruments in opposing hands, dramatically limits the flexibility of the surgeon's manipulative freedom.

The final, and least desirable manual methods of overcoming the drawbacks of separate instrumentation is to leave the tool which is not being utilized in the surgical field when it is not being actively used. Again, for obvious reasons, including impairing the visual field for the surgeon, it was known to be desirable to have a single tool which combines cauterizing and mechanical separation ability.

A substantial advance in the area of mechanical separation of tissues as well as cauterization was provided by the laser scalpel. Laser scapels utilize coherent light, often infrared light generated by a $CO_2$ or Yttrium-Aluminum-Garnet (YAG) power source, to ablate tissue away in a highly confined region. While the tremendous heat generated by the laser beam is more than substantial enough to cut through tissue as effectively as a scalpel (at least as efficiently as is necessary for many procedures) and also to cauterize surrounding tissues, the laser scalpel suffers from several important drawbacks as well.

Chief among these drawbacks is the fact that a laser scalpel which cuts by means of a coherent infrared beam is by definition invisible to the naked eye. Therefore, a surgeon must be able to manipulate the beam by watching the tissue surface which is literally burning before truly knowing the position of the "blade".

Second, but equally important is the inability to turn the cauterizing capacity off. More particularly, it is an important drawback of the laser scalpel that the cutting capacity is directly coupled to the heat generation, thus requiring at least some cauterization while cutting.

A related drawback of the laser scalpel, which is also a substantial drawback of present manual electrocautery instruments, is the imprecise nature of the cauterization. Both classes of surgical device cause substantial collateral damage to surrounding tissues. If cauterization is required near vital anatomical structures, great care must be taken to avoid damaging such tissues indirectly through the cauterization of the adjacent material. This problem is most severe in the field of microsurgery wherein many small vessels may be within a restricted field surgery, with only selected ones requiring cauterization.

In a sense, the cauterization instrument must combine the surgical precision of the microscalpel, the immediacy and strength of the laser, and also the selectivity of a separate instrument.

It is, therefore, a principle object of the present invention to provide a surgical instrument which combines precise tissue separation and cauterization ability within a single tool which enhances surgical flexibility.

It is further, an object of the present invention to provide a cauterizing cutting instrument which enhances visibility in the surgical field.

It is also an object of the present invention to provide a surgical instrument which permits greater precision in cauterization and cutting that instruments of the prior art.

It is an additional object of the present invention to provide an instrument which may be disposable, but which requires less wasted resources than present related surgical instruments.

SUMMARY OF THE INVENTION

The above-stated objects of the invention are achieved by the present invention which comprises a microsurgical electrocautery tool which is an advance over the microsurgical electrocautery tool set forth in the parent application U.S. Ser. No. 08/549,541, entitled "Coagulating Microknife System," filed Oct. 27, 1995, the specification of which is hereby incorporated by reference, further comprising new and novel features.

More particularly, the present invention, in a first set of embodiments, comprises a microsurgical electrocautery tool which achieves cauterization through the heating of the semiconducting substrate's cutting edge and/or structures disposed on surfaces of the substrate. In these embodiments, the present invention includes a semiconducting substrate which has been anisotropically etched to form at least one sharpened edge suitable for cutting, and a heating circuit mounted on a portion of the substrate which is in thermal association with the sharpened edge. The heating elements generally comprise at least one pair of electrically conductive bonding pads (first and second pads—said pads being electrically coupleable to an external voltage source), and at least one power bus line connecting corresponding pairs of pads.

In a first type of such a microcautery tool, the heating of the underlying substrate is provided by physically breaking the power bus line at intermittent points along its extent, coupling the exposed ends directly to the substrate surface, and causing the current to flow through the resistive semiconductor material (thereby causing a direct electrical heating of the substrate). This heating method provides excellent thermal control over the entire tool, however, if thermal differentiation between the two blade edges, i.e., the sharpened edge and the blunt edge, an alternative embodiment is preferable.

In a second embodiment of this type, which provides greater temperature differentiation, the tool comprises a semiconductor substrate having a sharpened edge, and power bus lines extending along the blade length on one side of the tool, wherein the power bus lines are electrically and thermally insulated from the substrate. The power bus lines couple serially with at least one resistive element (for example, a thin deposition layer) which is placed in the power bus path. The insulation of the power bus lines and the underlying substrate is provided by deposition layers provided during the semiconductor fabrication of the surface elements. The resulting structure provides excellent heating selectivity for different positions along the blade, as well as relative to the blunt edge.

In a third embodiment of this type, a strong temperature gradient is maintained relative to the sharpened and blunt edges via multiple power bus lines disposed on different surface portions of the tool. Either the direct substrate resistive heating, or the thermally isolated resistive heating elements may be utilized in conjunction with this alternative.

In yet another embodiment of this invention, the cauterizing structure may be alternatively intended to be spaced from the cutting edge, therein leaving the sharpened edge at a unheated (or much reduced heat) level, the power bus lines may be coupled to heating layers which are disposed over small etched pits formed in the surface of the tool. More particularly, the power buses are serially coupled in a circuit with heating layers which may be formed of any suitable material (such as one which may be deposited during microelectronics semiconductor wafer fabrication). The heating layers are structured such that they bridge etched pits formed in the surface of the semiconductor substrate and extending the length of the blade edge, thereby thermally insulating the heating elements from the tool material, further reducing the thermal equilibrating mechanisms.

Each of the above embodiments described, i.e., having resistive heating elements disposed on the surface of the tool or spaced above the surface of the semiconductor, can be further enhanced by providing a recess through the central portion of the semiconductor substrate. This recess may either extend fully through the substrate, or it may only extend partially through the surface. The recess is preferably disposed such that its axis is perpendicular to both the blade edge and the plane of the substrate surface. This recess further thermally insulates the cutting edge of the tool from the blunt edge. This permits further differentiation of the thermal characteristics of the tool. The combination of the recessed substrate and the heating element structure set forth above with respect to the embodiment wherein the heating elements comprise multiple heating element power bus circuit lines disposed on different portions of the tool, the temperature differential between the edges may be selectively maintained more completely insofar as the linear distance for thermal energy travel is greatly extended.

It shall also be appreciated that a recess which extends fully through the semiconductor substrate may also provide a line-of-sight advantage for the surgeon. If it is determined that the size of the recess must be so large as to threaten the structural viability of the tool, thin support ribs or columns of substrate material may be left to bridge across the space to provide mechanical strength. This lattice-work, if properly designed should not substantially interfere with the visual requirements of the surgeon. Carefully choosing the proper crystallographic etching planes can ensure that the cross-ribs retain sufficient strength.

Another optional enhancement comprises a means for detecting any damage to the cutting edge of the tool. While the tool is being used, the cutting edge may break or crack from internal or external stress. Due to the delicate nature of microsurgery, it will be useful for the operator of the tool to be able to detect when such damage occurs, so the tool can be replaced before it causes damage to the surrounding tissue. Therefore, additional embodiments of the present invention include an alarm circuit which comprises an external voltage source, first and second electrically conductive bonding pads, a detection wire, and an external means for alerting the operator to a discontinuity in the circuit.

Another optional enhancement comprises a means for measuring the temperature of the surfaces of the tool. Most particularly, due to the likelihood that an overheated cauterization surface could cause unwanted damage to tissue, or that an underheated cauterization surface could prevent the timely completion of the microsurgery, it will be useful for the operator of the tool to be able to measure the temperature of the cauterization surfaces. Additional embodiments of the present invention could therefore include a temperature sensing circuit which comprises an external voltage source, first and second electrically conductive bonding pads, a differential amplifier, a reference thermistor, a sensor thermistor, a connector wire, and a means for reporting the recorded temperature to the operator of the tool.

Another optional enhancement comprises an extension of the temperature sensing circuit, specifically an automated control means for maintaining a desired temperature of the cauterizing surfaces of the microsurgical electrocautery tool. If the temperature of the cauterizing surface rises to an undesirable level, the operator may want to reduce the temperature of the surface, instead of replacing the tool. It is possible to provide such a temperature controlling means by integrating the temperature sensing circuit described above into a closed loop temperature controller circuit which alters the current flow through the resistive heating elements according to the sensor feedback. In such a closed loop temperature controller circuit, the feedback loop is obtained through the thermal path from the heater elements to the sensor thermistor.

A further optional enhancement of the present invention comprises a suction means for removing excess tissue and fluid from the cutting and cauterizing area. Such a suction means comprises a pump, a channel between the cutting and cauterizing area and the pump through which the pump via suction pulls the excess tissue and fluid. The suction means could further comprise a reservoir or tank in which the removed tissue and fluid can be stored and/or recycled.

It shall further be understood that a variety of different tool shapes, i.e., blade conformations, recess sizes, and blunt edge designs, may be embodied as needed. A number of specific designs, and the particular methods of achieving such shapes is set forth more fully hereinbelow in the Detailed Description of the Preferred Embodiments.

BRIEF DESCRIPTION OF THE DRAWING

FIG. 1 is a plan view of a microsurgical electrocautery tool according to the first preferred embodiment;

FIG. 2 is a section view of a microsurgical electrocautery tool according to the first preferred embodiment;

FIG. 3 is a plan view of a microsurgical electrocautery tool according to the second preferred embodiment;

FIG. 4 is a first section view of a microsurgical electrocautery tool according to the second preferred embodiment;

FIG. 5 is a second section view of a microsurgical electrocautery tool according to the second preferred embodiment;

FIG. 6 is a plan view of a microsurgical electrocautery tool according to the fourth preferred embodiment;

FIG. 9 is a plan view of a microsurgical electrocautery tool according to the third preferred embodiment;

FIG. 10 is a section view of a microsurgical electrocautery tool according to the third preferred embodiment.

DETAILED DESCRIPTION OF THE PREFERRED EMBODIMENTS

Figure 7:
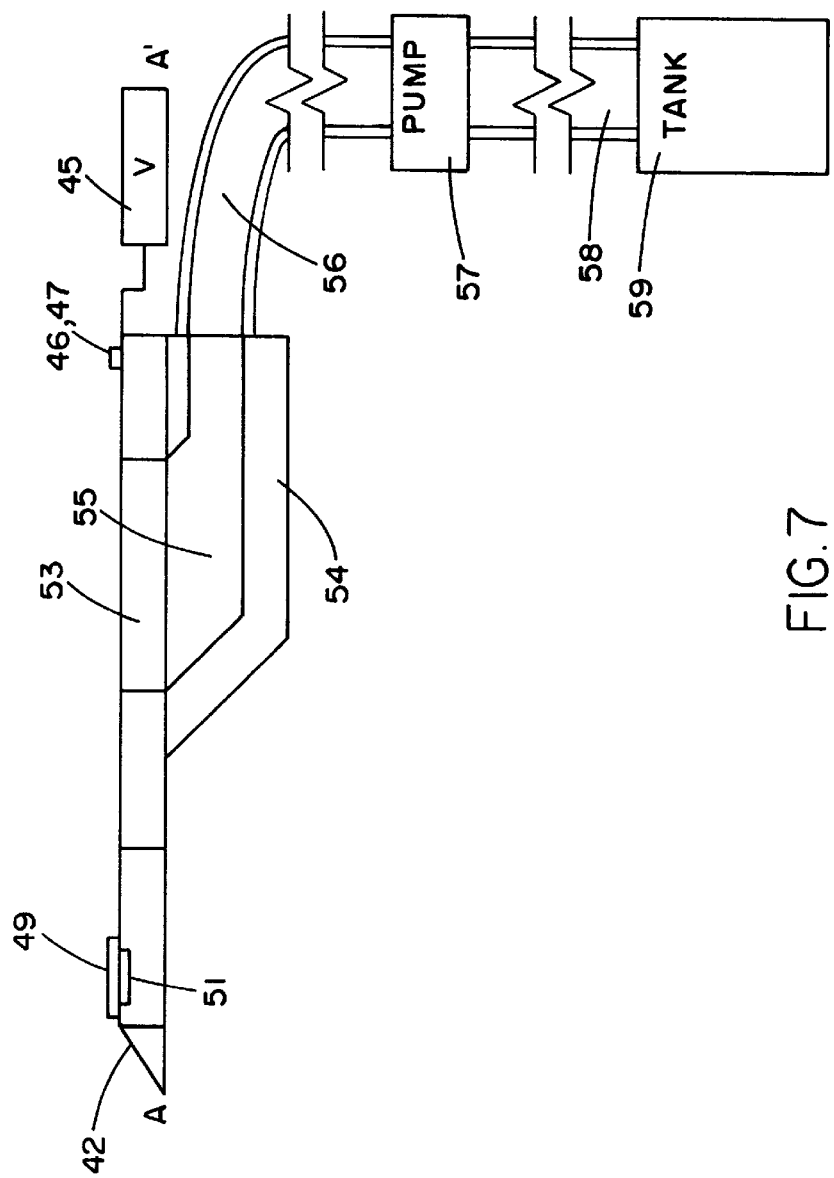
FIG. 7 is a first section view of a microsurgical electrocautery tool according to the fourth preferred embodiment.

A first preferred embodiment of the microsurgical electrocautery tool according to the present invention is illustrated in FIG. 1 and FIG. 2. The tool comprises a silicon wafer oriented in the (100) crystallographic plane which has been etched from a semiconducting substrate 21 to include at least one anisotropically etched sharpened outer edge 28. In a preferred embodiment, the outer edge of the substrate 21 has been anisotropically etched at an apex angle $\theta_1 = 54.7°$ to form an outer sharpened edge 28 suitable for cutting. The embodiment further includes recessed cavity, or window 22, which has been fully etched from the substrate semiconductor material, extending through the central portion of the tool. Thin support ribs 23 may be formed by appropriate masking of the etched central region of the tool during manufacturing, to provide structural support.

The cauterizing, or heating feature of this embodiment is provided by a heating circuit 29 which is mounted on a portion 30 of the substrate 21 which is in thermal association with the outer sharpened edge 28. This circuit 29 comprises an external voltage source 31, first and second electrically conductive bonding pads 32, 33, and a power bus line 34. An electric current generated by the external voltage source 31 is received at the first bonding pad 32 which is mounted on but electrically insulated from the substrate 21. (It shall be understood that the relative resistances of the bonding pads 32, 33 and the substrate semiconductor 21 will reduce the bleed-off current to insignificant levels, however, it is preferred that there be an electrically insulating film sandwiched between the bonding pads 32, 33 and the substrate. In an embodiment having a silicon semiconductor substrate the electrically insulating material may be a layer of silicon dioxide.) The operating voltage of the external voltage source 31 is less than 15 volts, preferably 5 volts. The first bonding pad 32 transfers the electric current to the power bus line 34 which is mounted on but electrically insulated from the substrate 21. The power bus line 34 first runs the length of the outer sharpened edge 28, then doubles back parallel to itself to return to the second bonding pad 33 which is mounted on but electrically insulated from the substrate 21. (As previously stated, this electrical insulation is not required for functionality, however, it is preferred for safety and for bonding purposes.) The second bonding pad 33 returns the electric current to the external voltage source 31, completing the circuit 29. The power bus line 34 includes intermittent breaks 35, and the open ends are coupled directly to the substrate 21. Therefore, at these intermittent break points 35 the electric current flows through the substrate 21, causing resistive heating of the semiconductor material. This electrically generated heat travels by thermal conduction through the substrate, and thus heats the outer sharpened edge 28 to temperatures as high as 300° Celsius, allowing it to be used as a cauterizing surface.

The window 22 provided in the central portion of the substrate provides thermal insulation between the heated sharpened edge 28 from the unheated blunt portion 42 of the tool (by virtue of a greater linear distance over which conduction of the resistive heating must extend.) The window 22 also provides an advantage insofar as a tool which does not include such a window would require more energy to heat the substrate material than the present embodiment requires. Further, the window 22 provides improved line-of-sight for the surgeon to more easily view the tissues in the cutting and cauterizing area. As shown in the present embodiment, if the size of the cavity must be so large as to threaten the structural viability of the tool, thin support ribs or columns of substrate material may bridge the space to provide mechanical strength without interfering with the line-of-sight advantage provided by the window 22. Additional embodiments of the present invention may obtain these and other advantages through the use of one or more partially or fully recessed cavities and the use of support ribs or columns.

Referring now FIGS. 3, 4 and 5 a second preferred embodiment of the nicrosurgical electrocautery tool according to the present invention is illustrated. This embodiment similarly comprises a semiconductor substrate which has been anisotropically etched to produce sharpened edges and a recess (window) through the central portion thereof In particular, this embodiment comprises a first sharpened edge 3 which defines an external blade, and a second sharpened edge 4 which defines an interior blade edge of the etched recess 2. As set forth above, with respect to the first embodiment, the present embodiment of the invention comprises a silicon wafer oriented in the (100) crystallographic plane which has been etched to include a recessed cavity, or window 2 which extends through the central portion of the tool. One outer edge of the substrate 1 has been anisotropically etched at an apex angle $\theta_1 = 54.7°$ to form an outer sharpened edge 3 suitable for cutting. One inner edge of the substrate 1 has also been anisotropically etched at an angle $\theta_1=54.7°$ to form an inner sharpened edge 4 suitable for cutting. In addition, the present embodiment comprises a pair of heating circuits, each of which are different. (It shall be understood that different heating element constructions are more efficient or preferable for heating different portions of the tool, depending upon the intended function of the corresponding portion.)

More particularly, a first heating circuit 5 is mounted on a portion 6 of the substrate 1 which is in thermal association with the outer sharpened edge 3. A second heating circuit 15 is mounted on a portion 16 of the substrate 1 which is in thermal association with the inner sharpened edge 4. The first heating element of the present embodiment is similar to that which was set forth above, with respect to the first embodiment (illustrated in FIGS. 1 and 2), i.e., resistive heating, by means of passing an electric current through the substrate material. More particularly, with reference to FIGS. 3, 4 and 5, the first circuit 5 comprises a first external voltage source 7, first and second electrically conductive bonding pads 8, 9 and a first power bus line 10. An electric current generated by the first external voltage source 7 is received at the first bonding pad 8 which is mounted on the substrate 1 (preferably electrically insulated therefrom). The operating voltage of the first external voltage source 7 is less than 15 volts, preferably 5 volts. The first bonding pad 8 transfers the electric current to the first power bus line 10 which is mounted on but electrically insulated from the substrate 1 except at intermittent break points 11. The first power bus line 10 first runs the length of the outer sharpened edge 3, then doubles back parallel to itself to return to the second bonding pad 9 which is mounted on the substrate 1 (again, preferably electrically insulated therefrom). The current returns to the external voltage source 7 through the second bonding pad 9, thus completing the first circuit 5. At the intermittent break points 11 the first power bus line 10 is physically broken, and the broken ends are coupled directly to the substrate 1. Therefore, at these intermittent contact points 11 electric current flows through the local region of the substrate 1 between the broken contacts, causing resistive heat to build, thus heating the outer sharpened edge 3 to temperatures as high as 300° Celsius, allowing it to be used as a cauterizing surface.

The second method of heating is also resistive heating, but not of the substrate material directly, but rather by the deposition of thin resistive elements into the circuit 15 disposed on the surface of the substrate. This method provides greater temperature differentiation between portions of the tool than may be supplied by the first method. More particularly, with respect to the present embodiment, the second heating circuit 15 is mounted on a portion 16 of the substrate 1 which is in thermal association with the inner sharpened edge 4. This second circuit 15 comprises a second external voltage source 17, third and fourth electrically conductive bonding pads 18, 19, a second power bus line 20, and at least one resistive element 21 (two elements 21 are shown), each of which comprises a thin deposition layer of resistive material which is mounted on the substrate 1 in such a way as to facilitate the easy transfer of thermal energy from the resistive element 21 to the substrate. (It shall be understood that if the resistive element is mounted directly onto the substrate surface, without any electrical insulation, the current will have the alternative path of the substrate material to travel through. Insofar as the purpose of the resistive elements 21 is to specifically control and isolate the heating provided, an electrical insulation must be provided if the resistivity of the elements are of the same order of magnitude, or greater than the substrate material, i.e., if the current would travel through the substrate more readily than through the resistive elements if given the opportunity.) An electric current generated by the second external voltage source 17 is received at the third bonding pad 18 which is mounted on the substrate 1 (and preferably electrically insulated therefrom). The operating voltage of the second external voltage source 17 is less than 15 volts, preferably 5 volts. The third bonding pad 18 transfers the electric current to the second power bus line 20 which is mounted on (and again, preferably electrically insulated from) the substrate 1. The second power bus line 20 first runs the length of the inner sharpened edge 4, then doubles back parallel to itself to return to the fourth bonding pad 19 which is mounted on (and again, preferably electrically insulated from) the substrate 1. The current returns to the second external voltage source 17 through the fourth bonding pad 19, completing the second circuit 15. The second power bus line 20 couples serially to each of the resistive elements 21 as shown. Electric current flows into the resistive elements 21 causing resistive heating of the inner sharpened edge 4 to temperatures as high as 600° Celsius, allowing it to be used as a cauterizing surface.

The window 2 has a plurality of functions. First, and most importantly for this embodiment, it makes possible the construction and use of the inner sharpened edge 4. Second, the window 2 helps to thermally insulate the heated sharpened edges 3, 4 from the unheated blunt portion 23 of the tool by virtue of the longer and narrower conduction path which the thermal energy must travel. As in the first preferred embodiment, the window 2 provides an advantage in that a tool which does not include such a window would require more energy to heat the substrate than the present embodiment requires. If designed correctly, partially or fully recessed cavities can also permit localized heating of designer-specified portions of the substrate. For example, in an embodiment such as the present embodiment, which includes more than one heating circuit, partially or fully recessed cavities can help to selectively maintain the temperature differential of the portions of the substrate having separate heating circuits, insofar as the linear distance for thermal energy travel is extended by the cavities. This will allow each region to operate individually and effectively at a different temperature. Third, as with the first embodiment, the window 2 provides improved line-of-sight for the surgeon to more easily view the cutting and cauterizing area. Again, if the size of the cavity must be so large as to threaten the structural viability of the tool, thin support ribs or columns of substrate material may bridge the space as illustrated in the first preferred embodiment to provide structural support without interfering with the improved line-of-sight advantage provided by the window 2. Similar to the present embodiment, additional embodiments of the present invention may also include a number of different heater regions, where each region is heated by any of the means described herein, and where the temperature of each region can be separately maintained. Thus, a single tool could have multiple uses, reducing the number of times the surgeon must switch tools during a given procedure.

Figure 8:
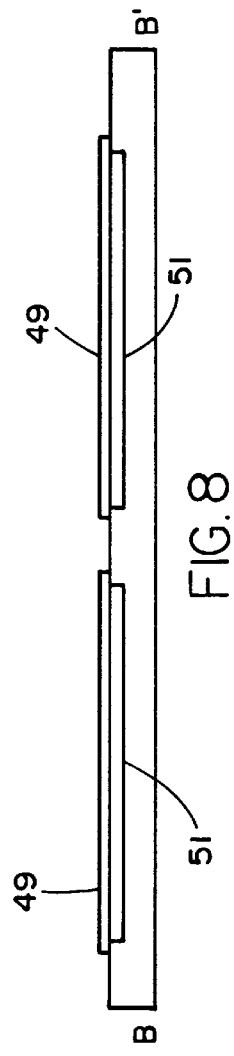
FIG. 8 is a second section view of a microsurgical electrocautery tool according to the fourth preferred embodiment.

Referring now to FIGS. 6, 7 and 8, a third alternative embodiment of the present invention is provided. This embodiment comprises a variety of alternative features, including a serrated blade, tissue and fluid suction action, and blade through resistive heating of deposition layers disposed over etched pits in the substrate material. More particularly, to obtain the serrated blade feature 42, the tool is anisotropically etched from a silicon wafer in which the (100) crystallographic plane is disposed parallel to the exposed flat top surface and wherein the <100> axis is oriented oblique to the edge line of the blade. This orientation causes an anisotropic etching of the substrate material at the blade line so as to cause the blade edge to have a serration. The specific angle of the serration is directly proportional to the oblique angle of the <100> axis relative to the blade line. In the present embodiment, one edge of the substrate 41 has been anisotropically etched such that angle of the <100> axis to the blade line is 90°, thus forming the regular form of the outer sharpened serrated edge 42.

With respect to the tissue and fluid suctioning feature, the present embodiment includes a suction means for removing excess tissue and fluid from the cutting and cauterizing area. The suction means comprises an anterior channel 53 in the body of the tool which extends through the tool, such that the front end of the anterior channel 53 opens toward the front or cauterization side of the tool, and the other back end of the anterior channel 53 opens toward the back of the tool. An additional rear structure 54 fixedly attached to the back of the tool comprises a posterior channel 55 which at one interior end is lined up with and serves to extend the anterior channel 53 from the back of the tool, and which at the other exterior end opens away from the tool as shown. A suction tube 56 is connected at a first end to the exterior end of the posterior channel 55, and connected at a second end to the suction orifice of a pump 57 which is located away from the tool. A reservoir tube 58 is connected at a first end to the discharge orifice of the pump 57, and at a second end to a reservoir tank 59. When the pump 57 is activated, excess fluid and tissue present at the cutting and cauterization site is suctioned through the anterior channel 53 in the tool, through the posterior channel 55 in the rear structure 54, through the suction tube 56, and into the suction orifice of the pump 57. The pump 57 then discharges the fluid and tissue material through its discharge orifice, through the reservoir tube 58, and finally into the reservoir tank 59. The reservoir tank 59 can be emptied at the surgeon's convenience. It is important to note that in additional embodiments of the present invention, the components of this suction means can be integrated into the tool structure itself, remain separate from but connected to the tool, or be partially integrated and partially separate. For example, the pump can be micromachined and fixedly housed in the tool structure itself. Further, a smaller reservoir tank can be fixedly housed in the tool structure itself, which would eliminate the need for external hoses and an external reservoir tank.

The heating circuit 43 of this embodiment is mounted on a portion 44 of the substrate 41 which is in thermal association with the serrated edge 42. This circuit 43 comprises an external voltage source 45, first and second electrically conductive bonding pads 46, 47, a power bus line 48, and two resistive heating layers 49, each of which is disposed over respective etched pits 51 formed in the surface of the tool. These etched pits 51 serve to thermally separate the underlying substrate 41 from the resistive heating layers 49. An electric current generated by the external voltage source 45 is received at the first bonding pad 46 which is mounted on but electrically insulated from the substrate 41. The operating voltage of the external voltage source 45 is less than 15 volts, preferably 5 volts. The first bonding pad 46 transfers the electric current to the power bus line 48 which is mounted on the substrate 41 (preferably electrically insulated therefrom). The power bus line 48 first runs the perimeter of the tool, then runs the length of the serrated edge 42. The power bus line 48 then runs the remainder of the perimeter to return to the second bonding pad 47 which is mounted on but electrically insulated from the substrate 41 (preferably electrically insulated therefrom). The electric current returns the to the external voltage source 45 via the second bonding pad 47, thus completing the circuit 43. The power bus line 48 couples serially to each of the resistive heating layers 49 as shown. Electric current flows to and from the resistive heating layers 49 heating them to temperatures as high as 600° Celsius, allowing them to be used as cauterizing surfaces.

Figure 11:
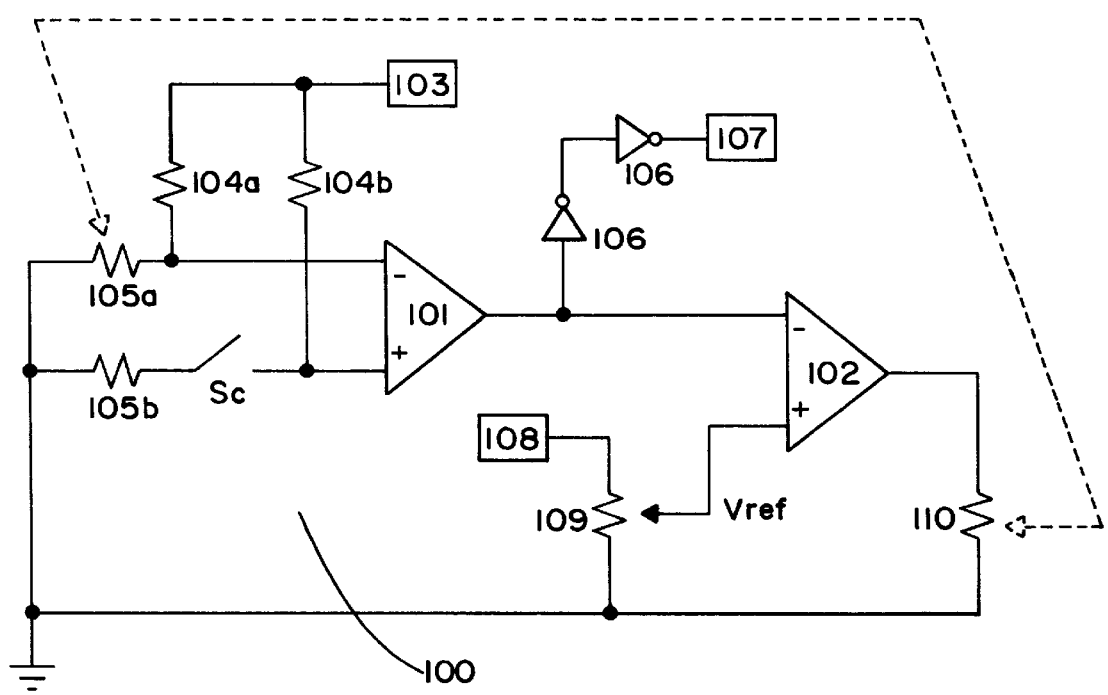
FIG. 11 is a schematic representation of the circuit includes in the microsurgical electrocautery tool according to the third preferred embodiment.

A fourth embodiment of the microsurgical electrocautery tool according to the present invention is illustrated in FIGS. 9, 10 and 11. In this embodiment, cauterization is achieved through the method described in the first embodiment, that is, through the resistive heating, by means of an electric current, of the substrate material itself. The tool comprises a silicon wafer oriented 20° off the (100) crystallographic plane which forms a semiconducting substrate 60 which functions as the body of the tool. One outer edge of the substrate 60 has been anisotropically etched at an apex angle of $\theta_2$=34.7° to form a long outer sharpened edge 61 suitable for cutting. One inner edge of the substrate 60 has been anisotropically etched at an apex angle of $\theta_3$=74.7° to form a short inner sharpened edge 62 suitable for cutting. The circuit 63 illustrated in schematic representation in FIG. 11 has been integrated into the semiconducting silicon substrate 60 using standard integrated circuits design and production techniques. The heat sensing aspect of the circuit 63 is represented by the box 64 shown in FIGS. 9 and 10 which is more fully described with respect to FIG. 11. Five electrically conductive bonding pads 65 allow the external components of the circuit 63 to be connected to the components of the circuit 63 which are integrated with the substrate 60. The components of the circuit 63 which heat the sharpened edges 61, 62 function as described in the first preferred embodiment. At the intermittent contact points 70 the power bus line 85 is physically broken, and the broken ends are coupled directly to the substrate 60. Therefore, between these intermittent contact points 70 electric current flows into the substrate 60, causing resistive heating of the semiconductor adjacent to the sharpened edges 61, 62 to temperatures as high as 300° Celsius, allowing them to be used as cauterizing surfaces.

The circuit 63 includes a means for measuring and controlling the temperature of the cauterizing surfaces 61, 62 of the tool. More particularly, due to the likelihood that an overheated cauterization surface could prevent the timely completion of the microsurgery by leading to unpredictable failures of the tool and/or causing greater tissue damage (cauterization) than expected, it will be useful for the surgeon to be able to measure the temperature of the cauterization surfaces 61, 62. Further, if the temperature of the cauterization surfaces 61, 62 rise to an undesirable level, the surgeon may want to reduce the temperature of the surfaces 61, 62, instead of replacing the tool.

The heat sensing and alarm circuit 100 of this embodiment is mounted on a portion 44 of the substrate 41 which is in thermal association with the serrated edge 42 (with a portion of the circuit being preferably mounted on the handle as set forth more fully hereinbelow). More particularly, this circuit 100 comprises a first voltage source 103 coupled to a pair of parallel reference resistors 104*a*, 104*b* (which are preferably equivalent in value). The reference resistors 104*a*, 104*b* are each coupled to respective inputs of a first differential amplifier 101. In series with the reference resistors 104*a*, 104*b*, but in parallel with the inputs of the first differential amplifier 101, are thermistors 105*a*, 105b, respectively. It is desirable for the first thermistor 105a to be located on the tool, preferably near the blade edge. The second thermistor 105b, however, should be located at a position which is far enough away from the heated substrate that its resistance value remains relatively constant. This position, as stated previously, may be on the handle of the tool itself When the thermistors 105a, 105b have similar values of resistance, such as prior to the heating of the tool, then the voltage drop across resistors 104a, 104b is equivalent, and the corresponding voltage differential across the first differential amplifier 101 is very small. As the tool heats up, however, the relative difference in the voltage drops across the two reference resistors 104a,104b becomes larger (because the resistance of the two thermistors 104a, 104b begins to differ with temperature). As this happens, the output of the differential amplifier 101 becomes larger. It shall be understood that it is preferable that the resistances of the reference resistors 104a, 104b and the thermistors 104a, 104b be of the same magnitude.

In order to detect breaks in the tool, the connection between the reference resistor 104b and the second thermistor 105b extends along the entire length of the tool, such that a break at any point would cause an instantaneous open circuit. Such an open circuit would have the effect of driving the differential voltage across the inputs of the first differential amplifier 101 to a high voltage, thus causing a high voltage output. The output of the first amplifier 101 is coupled to at least one high pass filter circuit 106, such as a schmidt trigger or other high threshold inverter circuit. In the event that the output of the first amplifier is large enough, which can only be achieved if the resistance of the first thermistor 105a is driven so far low that the voltage differential at the inputs of the first amplifier is driven above a set threshold (related to the amplification across the amplifier 101 and the threshold of the high pass filter 106) or if an open circuit occurs, thus pinning the output of the first amplifier 101 to its maximum (clearly over the threshold). This high pass filter 106 is coupled to an alarm mechanism 107, such as an LED or sound generating device, which signals the user that a malfunction or break has occurred.

During normal function of the tool, however, the output of the first amplifier 101 is coupled to one of the inputs of a second differential amplifier 102. The other input is coupled to a second voltage source 108 across a variable resistor 109. The output of the second amplifier drives the heating subcircuit 110 (conceptually represented here by a single resistive element). Inasmuch as the output voltage of the second amplifier 102 is proportional to the setting of the variable resistor 109, it is set such that the maximum output of the amplifier 102 is no greater than is necessary to provide the maximum power to the resistive element (heating circuit) 110. Heating of the blade, and thus the first thermistor 105a causes the output voltage of the first amplifier to increase, closer to the source 108 driven input of the second amplifier 102, thus decreasing the voltage output which drives the heating subcircuit, thereby diminishing the power dissipation in the resistive element 110 (the heating subcircuit).

More particularly, when the tool is first turned on, the difference between the input voltages to the first amplifier 101 is negligible (provided the resistivities are so chosen). This drives the output of the first amplifier 101 to a minimum. This minimal output of the first amplifier 101 causes the difference between the input voltages to the second amplifier 102 to go to its maximum (determined by the setting of the variable resistor 109). The heating subcircuit 110 is then maximally powered. Subsequent heating of the substrate alters the relative resistivity of thermistor 105a to thermistor 105b, thus increasing the input differential being applied to the first amplifier 101. This increase in input differential causes the output voltage of the first amplifier 101 to rise, thereby decreasing the relative voltage difference of the voltage inputs to the second amplifier 102. This decrease in the differential causes the output of the second amplifier 102 to drop, thereby reducing the power being supplied to the heating subcircuit 110. (It shall be understood that the amplitude of the inherent damped oscillations of the power to the heating subcircuit may be minimized if the reference thermistor 105a is placed near the power dissipation elements of heating subcircuit 110.)

While there have been described and illustrated certain specific embodiments of microsurgical electrocautery tool, it will be apparent to those skilled in the art that variations and modifications are possible without deviating from the broad spirit and principle of the present invention which shall be limited solely by the scope of the claims appended hereto.

We claim:

1. A surgical tool comprising:
   an etchable semiconductor material forming a substrate having at least one lateral edge, wherein at least one of said at least one lateral edge is sharpened to form a blade;
   means for sensing the temperature of said substrate, said means including an electrical circuit disposed on said substrate which circuit includes a thermistor; and
   said circuit including
      a voltage source having first and second terminals,
      electrically conductive material, forming a current carrying loop, which conducts from said first terminal to said second terminal of said voltage source, said loop including at least one discontinuity,
      at least one thermistor disposed in thermal association with said substrate and across said at least one discontinuity, whereby the current flowing through said circuit passes through said thermistor and is altered according to the resistance value of the thermistor, which value is related to the temperature of the substrate, and
      means for measuring said current in said current carrying loop.

2. A surgical tool comprising:
   an etchable material forming a substrate having at least one lateral edge, wherein at least one of said at least one lateral edge is sharpened to form a blade;
   said substrate including a recess formed in a central portion thereof; and
   at least one support rib extending accross said recess.

3. A surgical tool comprising:
   an etchable semiconductor material forming a substrate having at least one lateral edge, wherein at least one of said at least one lateral edge is sharpened to form a blade;
   means for heating said blade, said means including an electrical circuit disposed on said substrate;
   said electrical circuit further including
      a voltage source having first and second terminals,
      electrically conductive material disposed on a surface of said substrate for conducting a current from said first terminal to said second terminal of said voltage source, said electrically conductive material having at least one discontinuity therein,
      said at least one discontinuity forming at least two adjacent conduction end points, and at least one resistive element, wherein said at least two adjacent conduction end points are coupled in electrical current flowing relation to a corresponding one of said at least one resistive element, such that when said current flows through said circuit, current is directed by said electrically conductive material at said at least two conduction end points into and out of said corresponding at least one resistive element at said contact points thereof, whereby heat is generated by the resistive power dissipation of said corresponding at least one resistive element as said current flows therethrough; and wherein the substrate semiconductor material comprises recesses disposed beneath at least one of said at least one resistive element.

4. The surgical tool as set forth in claim 3, further including means for selectively controlling the temperature of said substrate, said temperature controlling means including a temperature sensing and feedback control circuit coupled to said means for heating said blade wherein said temperature sensing and feedback control circuit comprises;

a first subcircuit including,
a first resistive subassembly including at least two resistive elements in series, said first resistive subassembly being divisible into a first group and a second group of said at least two resistive elements, at least one of said resistive elements of one of said first and second groups being a thermistor coupled in thermal association with said substrate,
a second resistive subassembly including at least two resistive elements in series, said second resistive subassembly being divisible into a first group and a second group of said at least two resistive elements,
a first differential operational amplifier having first and second differential inputs and an output,
a first voltage source,
said first and second subassemblies each being coupled in parallel between said first voltage source and ground,
said first and second resistive subassemblies being electrically coupled to said first and second differential inputs of said first differential operational amplifier, respectively, wherein said coupling occurs between said first and second groups of each resistive subassembly and the respective input; and a second subcircuit including,
a second differential operational amplifier having first and second differential inputs and an output,
a second voltage source electrically coupled to said first differential input of said second differential operational amplifier,
said output of said first differential operational amplifier being electrically coupled to said differential input of said second differential operational amplifier,
wherein said output of said second differential operational amplifier forms the voltage source of said heating circuit,
wherein the resistance of the unheated thermistor causes the differential voltage across the first and second inputs of the first differential operational amplifier to be driven to a low value, whereby the output of the first differential operational amplifier provides a low voltage value to the second input of the second differential operational amplifier, such that the differential voltage across the first and second inputs of the second differential operational amplifier is driven high, whereby the output of the second differential operational amplifier is driven high and the voltage provided to the heating circuit is commensurately high, and
wherein resistance of the heated thermistor causes the differential voltage across the first and second inputs of the first differential operational amplifier to be driven to a high value, whereby the output of the first differential operational amplifier provides a high voltage value to the second input of the second differential operational amplifier, such that the differential voltage across the first and second inputs of the second differential operational amplifier is driven low, whereby the output of the second differential operational amplifier is driven low and the voltage provided to the heating circuit is commensurately low.

* * * * *